(12) United States Patent
Mercier et al.

(10) Patent No.: US 9,363,863 B2
(45) Date of Patent: Jun. 7, 2016

(54) ELECTROMAGNETIC RADIATION EMITTER IDENTIFICATION APPARATUS AND ASSOCIATED METHODS

(71) Applicant: Biozone Scientific International, Inc., Orlando, FL (US)

(72) Inventors: Matthew Mercier, Windermere, FL (US); Ari Ahola, Windermere, FL (US); Adam T Anthony, Windermere, FL (US); Hal Gunner, Lady Lake, FL (US)

(73) Assignee: Biozone Scientific International, Inc., Melbourne, FL (US)

( * ) Notice: Subject to any disclaimer, the term of this patent is extended or adjusted under 35 U.S.C. 154(b) by 0 days.

(21) Appl. No.: 14/303,025

(22) Filed: Jun. 12, 2014

(65) Prior Publication Data
US 2015/0366030 A1    Dec. 17, 2015

(51) Int. Cl.
| | |
|---|---|
| *H05B 37/02* | (2006.01) |
| *H01J 61/56* | (2006.01) |
| *H01J 17/28* | (2006.01) |
| *H01J 17/36* | (2006.01) |
| *H05B 33/08* | (2006.01) |
| *A61L 2/10* | (2006.01) |
| *H01J 5/50* | (2006.01) |
| *H05B 41/36* | (2006.01) |

(52) U.S. Cl.
CPC ............. *H05B 37/02* (2013.01); *H01J 17/28* (2013.01); *H01J 17/36* (2013.01); *H01J 61/56* (2013.01); *H05B 33/0806* (2013.01); *H05B 33/0884* (2013.01); *A61L 2/10* (2013.01); *C02F 2201/326* (2013.01); *H01J 5/50* (2013.01); *H05B 41/36* (2013.01)

(58) Field of Classification Search
CPC ........ A61L 2/10; C02F 2201/326; H01J 5/50; H01J 61/56; H01J 17/36; H01J 17/28; H05B 37/02; H05B 33/08; H05B 33/0806; H05B 33/0884
USPC ................ 315/49, 51, 291, 307, 308, 312
See application file for complete search history.

(56) References Cited

U.S. PATENT DOCUMENTS

| | | | |
|---|---|---|---|
| 5,679,944 A | 10/1997 | Cusey et al. | |
| 6,414,449 B1 | 7/2002 | Hui et al. | |
| 6,809,652 B1 * | 10/2004 | Baxter | ................ H05B 41/36 340/332 |
| 6,906,337 B2 | 6/2005 | Wedekamp | |
| 7,759,873 B2 | 7/2010 | Mastenbroek et al. | |
| 8,032,181 B2 | 10/2011 | Hauck et al. | |
| 8,311,892 B2 | 11/2012 | Junger | |
| 8,315,876 B2 | 11/2012 | Reuss | |
| 8,344,649 B2 | 1/2013 | Siessegger et al. | |

(Continued)

FOREIGN PATENT DOCUMENTS

| | | |
|---|---|---|
| DE | 19640625 A1 | 4/1998 |
| DE | 202005003285 U1 | 8/2006 |

(Continued)

*Primary Examiner* — Jimmy Vu
(74) *Attorney, Agent, or Firm* — Kelly G. Swartz; Widerman Malek, PL

(57) ABSTRACT

The invention relates to an apparatus and associated method for emitting electromagnetic radiation. The apparatus has at least one electromagnetic radiation emitter and a base. The base has four electrical contacts and an identification device. Two of the electrical contacts are in electrical communication with the at least one electromagnetic radiation emitter. The other two electrical contacts are in electrical communication with the identification device.

35 Claims, 6 Drawing Sheets

(56) References Cited

U.S. PATENT DOCUMENTS

| | | |
|---|---|---|
| 8,510,171 B2 | 8/2013 | Pederson et al. |
| 8,558,459 B2 | 10/2013 | Busse et al. |
| 8,612,771 B2 | 12/2013 | Zollinger et al. |
| 2004/0113102 A1 | 6/2004 | Wedekamp |
| 2007/0234427 A1 | 10/2007 | Gardner et al. |
| 2008/0218171 A1 | 9/2008 | Keith et al. |
| 2009/0289582 A1 | 11/2009 | Armitage et al. |
| 2012/0169237 A1 | 7/2012 | Carrasco et al. |
| 2012/0235595 A1 | 9/2012 | Busse et al. |
| 2012/0239527 A1 | 9/2012 | Cheney et al. |
| 2013/0170327 A1 | 7/2013 | Peters et al. |
| 2013/0238471 A1 | 9/2013 | Maraz et al. |

FOREIGN PATENT DOCUMENTS

| | | |
|---|---|---|
| DE | 102009011765 A1 | 10/2010 |
| EP | 0869640 A1 | 7/1998 |
| EP | 1598949 A2 | 11/2005 |
| EP | 1458223 B1 | 10/2008 |
| EP | 2055349 A2 | 6/2009 |
| EP | 2259661 A2 | 12/2010 |
| EP | 1878322 B1 | 2/2013 |
| JP | 2009004241 A3 | 2/2009 |

* cited by examiner

ELECTROMAGNETIC RADIATION EMITTER IDENTIFICATION APPARATUS AND ASSOCIATED METHODS

FIELD OF THE INVENTION

The present invention relates to the field of electromagnetic emission devices. More specifically, the present invention relates to electromagnetic radiation emitters, including, but not limited to, visible, ultraviolet, and infrared lamps, LEDs, X-Ray emission tubes, arc tubes, fluorescent lamps, or the like, which include an identification device.

BACKGROUND OF THE INVENTION

Electromagnetic emitters are traditionally paired with a specific electrical supply or control system. The characteristics of the various emitters differ. By properly pairing electromagnetic emitters with appropriate supply or control systems, the operation or effectiveness of the electromagnetic emitter can be improved or optimized.

By way of example of a particular electromagnetic emitter, low pressure mercury lamps have traditionally been used as UV radiation sources. These lamps emit UV light of a wavelength which is suitable for destroying microorganisms in fluids. The degree of disinfection of the fluid is a function of the UV dose applied. The characteristics of different lamps differ and therefore emit differing levels of UV light suitable for destroying microorganisms.

As a result, there exists a need for an apparatus that can be identified as suitable for use with a particular system requiring specific electromagnetic wavelength characteristics. The system may operate only when the electromagnetic emitter is identified as suitable for the system. This may prevent activation of unauthorized electromagnetic emitters, which may have unknown electromagnetic wavelength characteristics or operation of systems with unauthorized electromagnetic emitters.

SUMMARY OF THE INVENTION

With the foregoing in mind, embodiments of the present invention are related to a method and apparatus for identifying and controlling an electromagnetic radiation emitter.

According to an embodiment of the present invention, electromagnetic radiation emitters, which emit radiation in the spectrum from 1.0 mm to 1.0 pm wavelengths, may be utilized. These electromagnetic radiation emitters may emit electromagnetic energy by energizing gas filled envelopes. Additionally, closer to the 1.0 mm end of the spectrum, electromagnetic energy can be produced using resistive elements, such as, by way of example, and not as a limitation, an infrared heater. Toward the 1.0 pm end of the spectrum, electromagnetic energy may be produced, by way of example, and not as a limitation, by focusing an electron beam on a metallic target and producing x-ray photons.

The electromagnetic radiation emitter device may have a base and an envelope. The base may contain electrical contacts, which create electrical connections to a controller that provides or receives electrical communication to or from the electromagnetic radiation emitting device. Additionally, the base may contain an identification device. The controller may send a query to the identification device, which the identification device may respond to by sending a response, which may be an electronic signature, to the controller.

The controller may have a query module that is in electrical communication with the identification device and creates the query that is sent to the identification device. The identification device may be an electronic component having an identifying electronic signature that is provided to the query module in response to receiving a query.

The controller may include an electronic signature detection module, which may receive or analyze the response received from the identification device. Upon analyzing the response, the electronic signature detection module may determine whether the identification device is authorized or unauthorized depending upon whether the response corresponds with the anticipated electronic signature of the identification device. The identification device, and therefore the electromagnetic radiation emitter itself, may be unauthorized if the response does not correspond with the electronic signature or if no electronic signature is received.

The envelope may emit electromagnetic radiation. In certain embodiments, a ballast may be directed by the controller to apply a voltage signal to energize the envelope only when the electromagnetic radiation emitter is identified as authorized. In some embodiments, the controller may provide a negative energizing control signal to the ballast, preventing the ballast from outputting a high voltage signal, and therefore preventing the envelope from emitting electromagnetic radiation, when the response received from the identification device is not as expected. In some embodiments, the controller may refrain from providing a positive energizing control signal to the ballast, preventing the ballast from outputting a high voltage signal, and therefore preventing the envelope from emitting electromagnetic radiation.

The apparatus may also include an alerting device, which may provide a sensory indication of whether or not the electromagnetic radiation emitter is authorized. The controller may send a control signal to the alerting device to alter or control the alert status of the alerting device dependent upon the response to the query.

The apparatus may also include a fan, which may be utilized to circulate fluid and expose it to the radiation produced by the emitter. The controller may send a fan control signal to the fan to alter or control the state of the fan dependent upon the response to the query.

DETAILED DESCRIPTION OF THE PREFERRED EMBODIMENT

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Electromagnetic emitters in the spectrum from 1.0 mm to 1.0 pm wavelength may emit electromagnetic energy by energizing gas filled envelopes. Additionally, closer to the 1.0 mm end of the spectrum, electromagnetic energy can be produced using resistive elements, such as, by way of example, and not as a limitation, infrared heaters. Toward the 1.0 pm end of the spectrum, electromagnetic energy may be produces, by way of example, and not as a limitation, by utilizing an x-ray photon emitter. Electromagnetic emitters may also emit energy using a light emitting diode.

Figure 1:
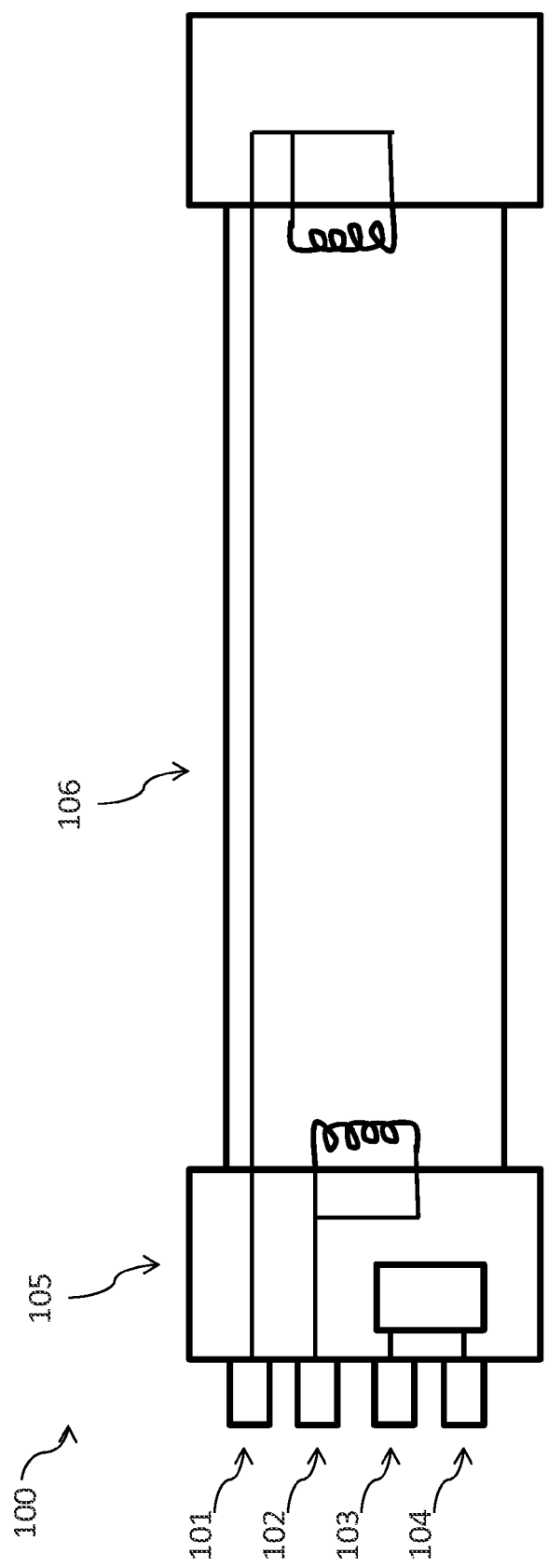
FIG. 1 is one embodiment of the apparatus.

Referring to FIG. 1, an apparatus for emitting electromagnetic radiation 100 is depicted. The apparatus may comprise a base 105 and an electromagnetic radiation emitter. In one embodiment, as depicted in FIG. 1, the electromagnetic radiation emitter may comprise an envelope 106. The base 105 may contain the electrical contacts to create electrical connections to a control unit that provides or receives electrical communication to or from the apparatus for emitting electromagnetic radiation 100. Additionally, the base 105 may contain an identification device. The identification device may provide an electronic signature to the controller. The identification device may be electrically connected to and may be in electrical communication with a third electrical contact 103 and a fourth electrical contact 104. The envelope 106 may be filled with gas and metallic elements and the emitter may produce electromagnetic emissions when exposed to ionizing energy. In some embodiments, the envelope 106 may be filled with gas and metallic elements that may produce electron emissions when exposed to ionizing energy. In one embodiment, the envelope 106 may be filled with low pressure mercury vapor. In one embodiment, the envelope may emit ultraviolet radiation. The envelope may be connected to a first electrical contact 101 and a second electrical contact 102 to allow a voltage to be introduced to the chamber created by the envelope 106. The voltage may allow radiation to be emitted from the envelope 106.

The embodiment depicted in FIG. 1 utilizes a cold start method which requires only two electrical contacts to create electromagnetic emission from the envelope 106. Such an embodiment may be particularly desirable in environments in which the radiation emitter is not frequently cycled between activated and deactivated states.

The embodiment depicted in FIG. 1 allows for the introduction of an identification device into the radiation emitter while maintaining a four electrical contact configuration. By utilizing a cold start method, two electrical contacts are utilized by the radiation emitter freeing the remaining two electrical contacts for use by an identification device. This may be particularly advantageous in environments in which it is costly or impractical to replace existing fittings for radiation emitting devices.

Such an apparatus may be utilized in a sanitation device. The radiation emitter may emit a UV light with characteristics well suited to destroying microorganisms. The sanitation device may energize the radiation emitter only when the identification device indicates that the radiation emitter is of a type well suited for the sanitation apparatus's purpose. When the identification device is not recognized by the sanitation apparatus, the sanitation apparatus may not activate the radiation emitter or may provide a sensory indicator that the radiation emitter is not recognized by the sanitation apparatus.

In such an embodiment, the sanitation apparatus may include a fan, which may be beneficial in circulating the microorganism destroying properties of plasma created by the radiation emitter throughout a fluid. The fan may also circuit fluid about the radiation emitter.

Figure 2:
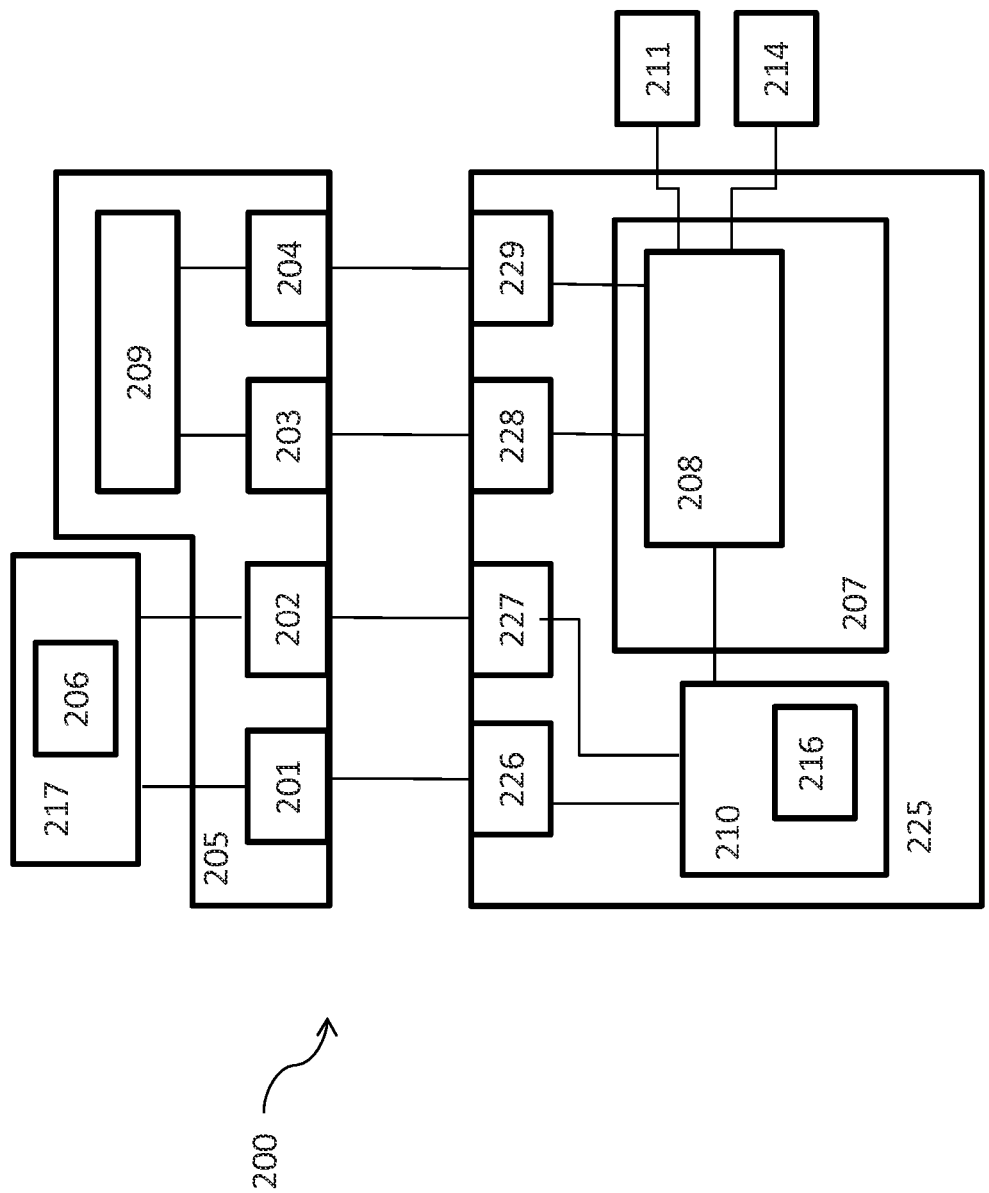
FIG. 2 is a block diagram of one embodiment of the apparatus.

FIG. 2 depicts a block diagram of the apparatus 200, including a control unit 225. The control unit may comprise a controller 207, a first electrical contact receptor 226, a second electrical contact receptor 227, a third electrical contact receptor 228, and a fourth electrical contact receptor 229. The first, second, third, and fourth electrical contact receptors 226, 227, 228, 229 may engage the first, second, third, and fourth electrical contacts 201, 202, 203, 204. The contacts may mount in the receptors and be unmounted. The receptors 226, 227, 228, 229 may be in a physical configuration to allow for correct alignment with respective contacts 201, 202, 203, 204 and prevent an incorrect mating. The base 205 may be removed from the connection to the control unit 225 and replaced.

The controller 207 may comprise a query module 208 in electrical communication with the third and fourth electrical contact receptors 228, 229. The query module 208 may send a query to the identification device 209. The identification device 209 may send a response to the query module 208. The identification device 209 may be an electronic component and the electronic component may have an electronic signature that is provided to the query module 208 in response to receiving a query. The identification device may be, by way of example, and not as a limitation, a silicon serial number chip, an RC circuit, a PROM, a circuit having a resistance value, an inductive load, a magnet, or the like. The query may take many forms depending on the requirements of the identification device 209. In embodiments in which the identification device 209 is a silicon serial number chip or a PROM, the query module 208 may send an electronic signal to the identification device 209 instructing the identification device 209 to transmit a serial number or a programmed identifier. The anticipated response of the identification device 209 to the query may be the electronic signature of the identification device. The actual signal received by the query module 208, or sent by the identification device 209, may be the response of the identification device 209.

By way of example, and not as a limitation, in embodiments in with the identification device 209 is a silicon serial number chip, the electronic signature may be the serial number associated with the silicon serial number chip. By way of example, and not as a limitation, in embodiments in with the identification device 209 is a resister-capacitor (RC) circuit, the electronic signature may be the charge or discharge time of the circuit. By way of example, and not as a limitation, in embodiments in with the identification device 209 is a circuit having a resistance value, the electronic signature may be the resistance value of the circuit. By way of example, and not as a limitation, in embodiments in which the identification device 209 is a programmable read-only memory (PROM), the electronic signature may be the pre-programmed identifier that may be read from the PROM.

The query module 208 may receive or analyze the response received from the identification device 209 and determine whether the identification device 209 is authorized or unauthorized. The identification device 209 may be authorized if the response corresponds with the electronic signature of the identification device 209. The identification device 209 may be unauthorized if the response does not correspond with the electronic signature or if no electronic signature is received.

In one embodiment, as depicted in FIG. 2, a ballast 210 may apply a voltage signal to the first and second electrical contact receptors 226, 227. The first and second electrical contact receptors 226, 227 are electrically connected to the first and second electrical contacts 201, 202, which are electrically connected to the at least on electromagnetic radiation emitter. In embodiments in which an envelope 206 is present, the voltage applied to the electromagnetic radiation emitter may energize the gas within the envelope 206.

In one embodiment, an arc controller 216 may provide a high voltage signal to be applied across the first and second electrical contacts 201, 202 to create an arc within the envelope 206. The controller 207 may be electrically connected to a ballast 210. When the ballast 210 receives an energizing control signal from the controller 207, the ballast 210 may output a high voltage signal to the emitter 217, through the first and second electrical contacts 201, 202, causing the emitter 217 to produce electromagnetic radiation.

The query module 208 may control the energizing control signal sent to the ballast 210. The query module 208 may be in electrical communication with the ballast 210. The query module 208 may generate the energizing control signal provided to the ballast 210. The ballast 210 may output a high voltage signal in response to the energizing control signal provided by the query module 208. The query module 208 may provide a negative energizing control signal to the ballast 210, or refrain from providing a positive energizing control signal, preventing the ballast from outputting a high voltage signal, and therefore preventing the emitter 217 from producing electromagnetic radiation, when the response received from the identification device 209 is not as anticipated. The query module 208 may provide a positive energizing control signal to the ballast 210, causing the ballast 210 to output a high voltage signal, or allowing the ballast 210 to output a high voltage signal provided some other condition is met, when the response received from the identification device 209 indicates that the identification device 209 associated with the envelope 206 is authorized.

The apparatus may also include an alerting device 211. The alerting device may be, by way of example, and not as a limitation, an LED, a piezo buzzer, a device emitting light, a device emitting sound, a liquid crystal display, a device capable of displaying a message, or the like. The alerting device 211 may be in electrical communication with the query module 208. The alerting device 211 may have an alert status. In one embodiment, the alert status may be positive or negative. The alert status may be associated with the state of the alerting device 211 and may vary based on the nature of the alerting device 211. By way of example, and not as a limitation, in an embodiment in which the alerting device is an LED, the positive alert status may be on and the negative alert status may be off. In another embodiment in which the alerting device is a pair of LEDs, the positive alert status may be that a blue LED is illuminated and the negative alert status may be that a red LED is illuminated. In embodiments in which the alerting device 211 is a device that may emit sound, the positive alert status may be deactivated and the negative alert status may be periodically, intermittently, or continuously, activated.

The query module 208 may send an alert control signal to the alerting device 211 to alter or control the alert status of the alerting device 211. The alert control signal may be determined by the response to the query. If the response indicates that the identification device 209 is an authorized device, the alert control signal may place the alerting device in a positive alert status. If the response indicates that the identification device 209 is an unauthorized device, the alert control signal may place the alerting device in a negative alert status.

The apparatus 200 may also include a fan 214. The fan 214 may be utilized to circulate fluid in relation to the at least one electromagnetic radiation emitter 217. The query module 208 may send a fan control signal to the fan 214 to alter or control the state of the fan 214. The fan control signal may be determined by the response to the query. If the response indicates that the identification device 209 is an authorized device, the fan control signal may activate the fan 214. If the response indicates that the identification device 209 is an unauthorized device, the fan control signal may prevent the fan 214 from activating.

The ballast control signal may be created by the query module 208 and provided to the ballast 210. The query module 208 may provide a positive energizing control signal to the ballast 210, causing the ballast 210 to output a high voltage signal, or allowing the ballast 210 to output a high voltage signal provided some other condition is met, when the response received from the identification device 209 indicates that the identification device 209 associated with the at least one electromagnetic radiation emitter 217 is authorized.

Figure 3:
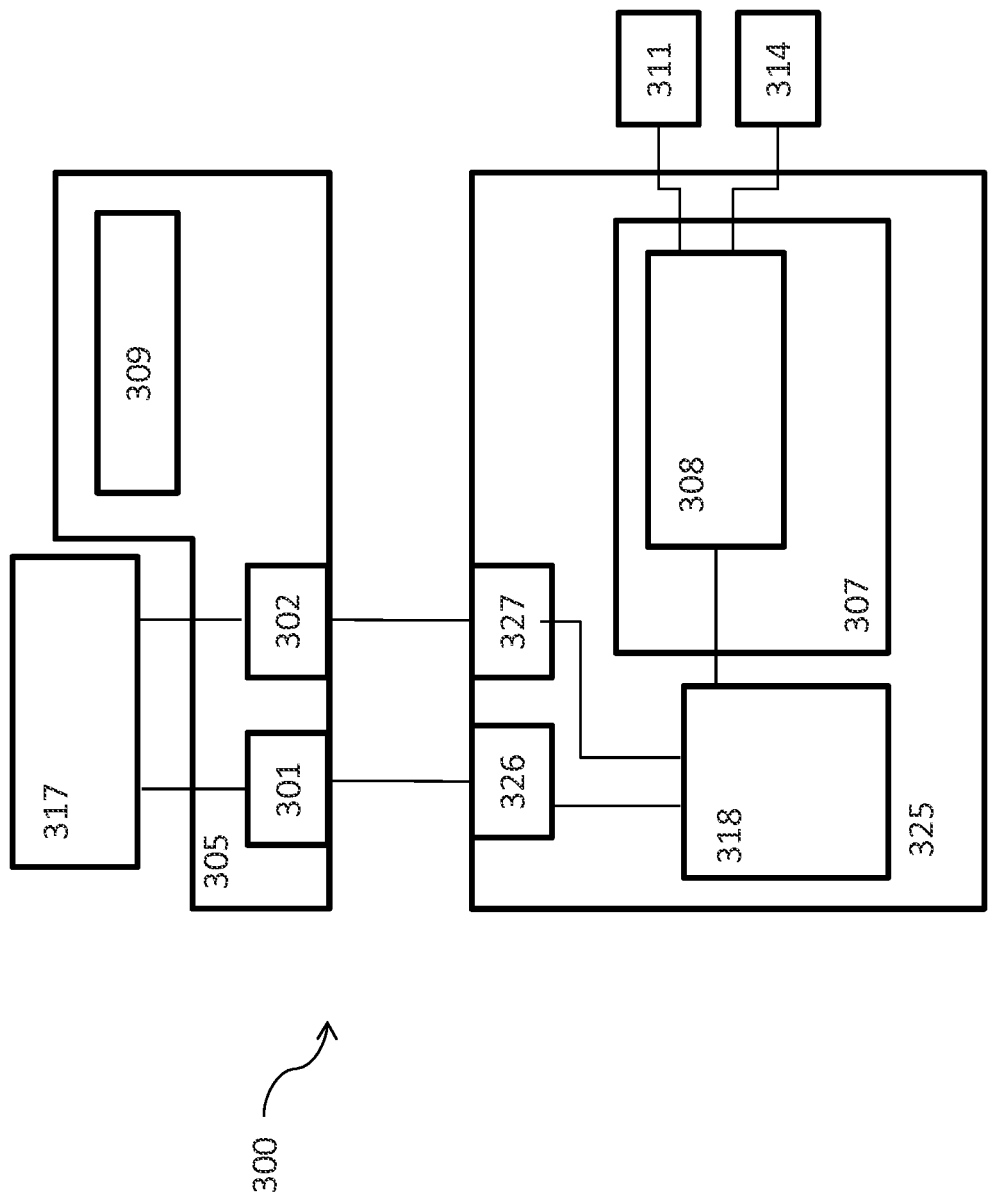
FIG. 3 is a block diagram of one embodiment of the apparatus.

Referring to FIG. 3, an apparatus for emitting electromagnetic radiation 300 is depicted. The apparatus may comprise a base 305 and at least one electromagnetic radiation emitter 317. The base 305 may contain the electrical contacts 301, 302 to facilitate electrical connections to a control unit 325 that provides or receives electrical communication to or from the base 305. Additionally, the base 305 may contain an identification device 309. The identification device 309 may provide a status to a query module 308 contained within the controller 307. The query module 308 may be able to determine the status of the identification device 309 when the base 305 is in close proximity to the control unit 325, even though the query module may not be in direct electrical communication with the identification device 309.

The electromagnetic radiation emitter 317 may be an LED, oLED, any device capable of emitting electromagnetic radiation, or the like. In such an embodiment, as shown in FIG. 3, there may not be an envelope. The electromagnetic radiation emitter 317 may be connected to a first electrical contact 301 and a second electrical contact 302 to allow a voltage to be applied to the electromagnetic radiation emitter 317. An electromagnetic radiation emitter driving circuit 318 may be located in the control unit 325. The electromagnetic radiation emitter driving circuit 318 may provide the voltage necessary to operate the electromagnetic radiation emitter 317. The query module may provide a control signal to the electromagnetic radiation emitter driving circuit 318. The output of the electromagnetic radiation emitter driving circuit 318 may be in electrical communication with the first and second electrical contact receptors 326, 327.

The output of the electromagnetic radiation emitter driving circuit 318 may depend upon the control signal received by it from the query module 308. The control signal sent to the electromagnetic radiation emitter driving circuit 318 from the query module 308 may depend upon the status of the identification device 309. When the query module 308 determines that the identification device 308 is present or authorized, the query module 308 may send a control signal to the electromagnetic radiation emitter driving circuit 318 indicating that the at least one electromagnetic radiation emitter 317 may be activated.

Figure 4:
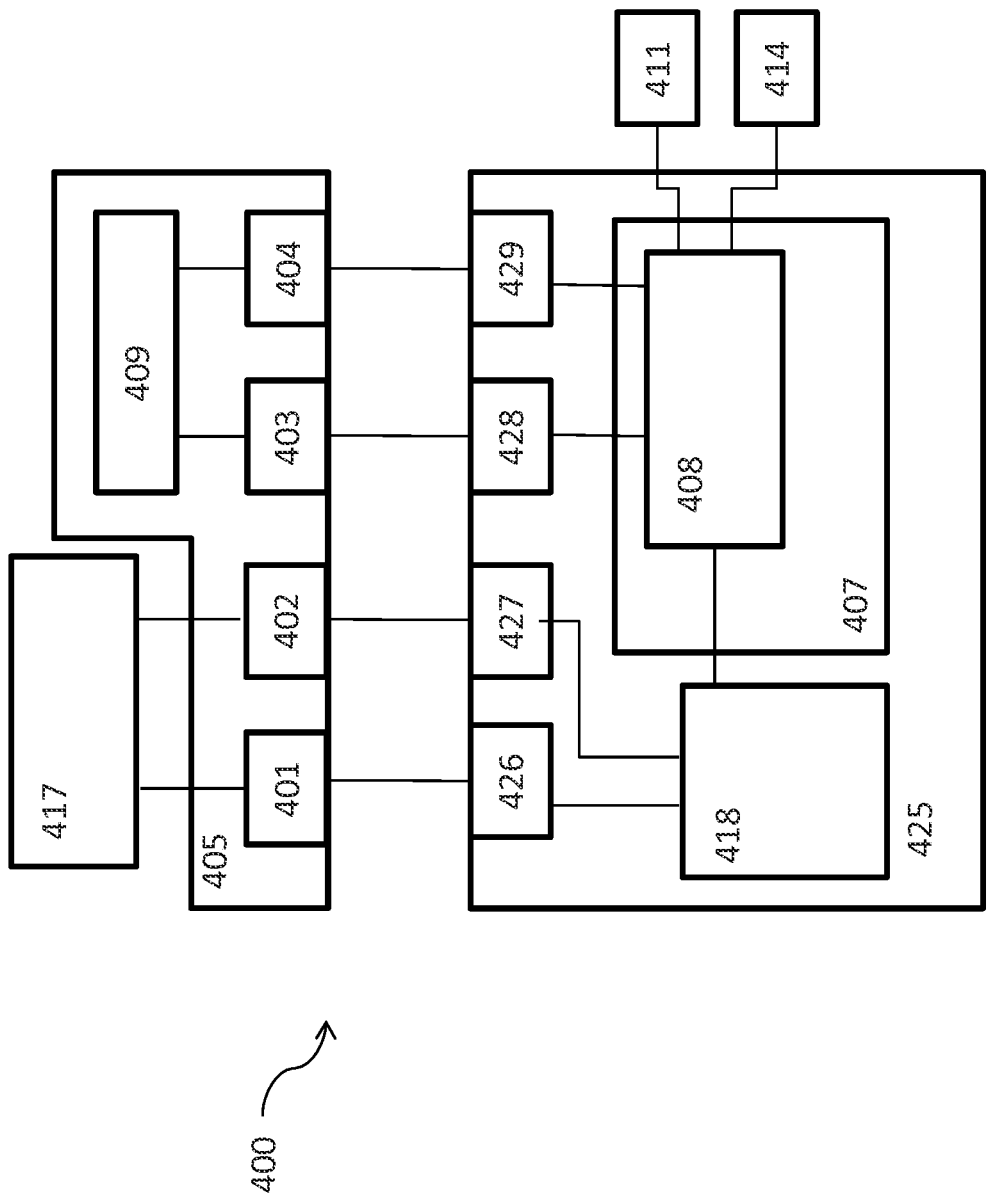
FIG. 4 is a block diagram of one embodiment of the apparatus.
Figure 5:
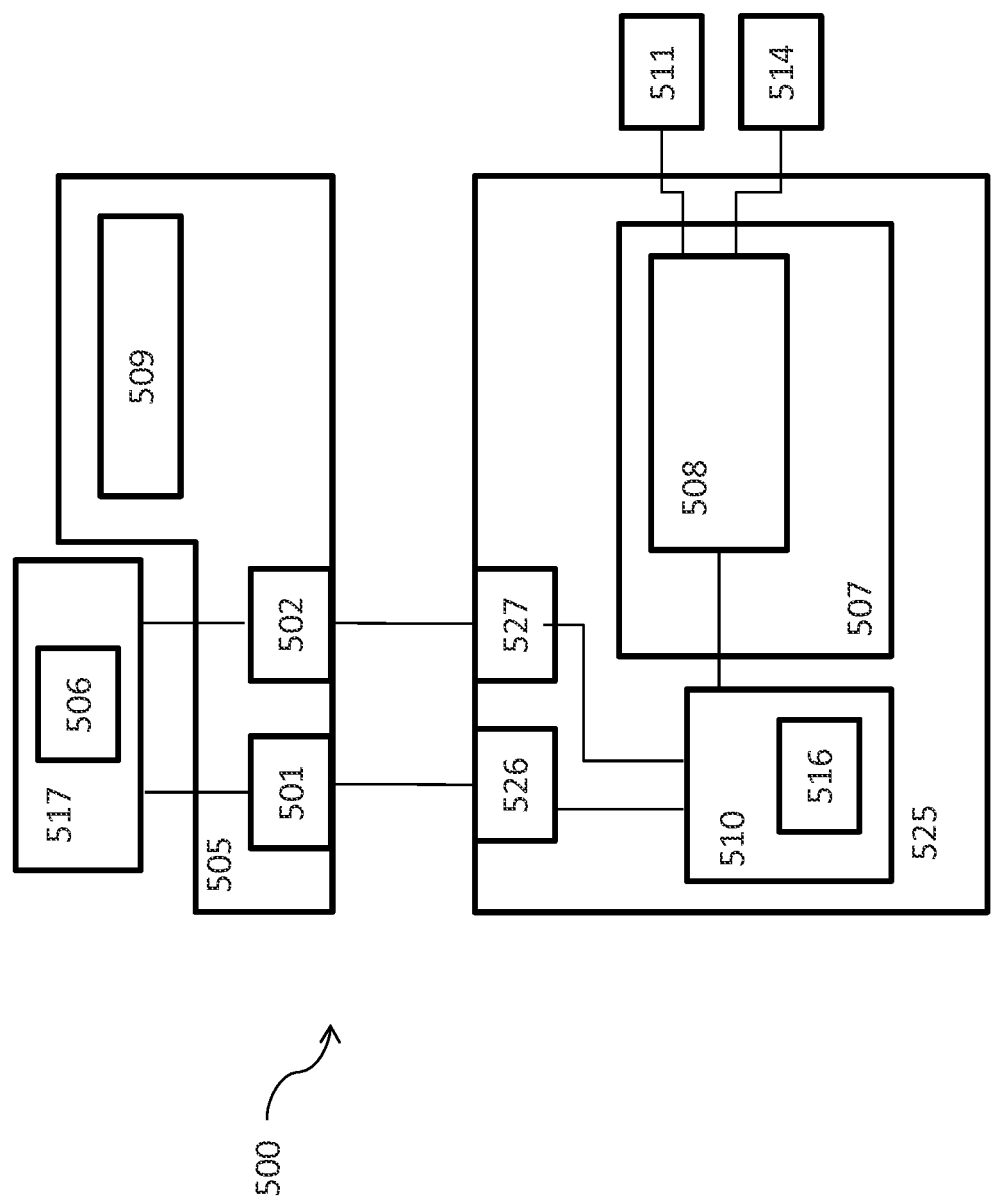
FIG. 5 is a block diagram of one embodiment of the apparatus.

As depicted in FIGS. 3 and 5, there are no third or fourth electrical contacts or electrical contact receptors. Such a configuration may be present in embodiments utilizing a ballast 510, as depicted in FIG. 5, or an electromagnetic radiation emitter driving circuit 318, as depicted in FIG. 3. Likewise an embodiment with either a ballast 510 or an electromagnetic radiation emitter driving circuit 318 may be configured with or without third or fourth electrical contacts and electrical contact receptors, as depicted in FIGS. 2-5. The presence or absence of a ballast 510 or electromagnetic radiation emitter driving circuit 318 is independent of the presence or absence of third or fourth electrical contacts and electrical contact receptors. The presence or absence of third or fourth electrical contacts and electrical contact receptors is dependent upon the type of identification device that is utilized in a particular embodiment.

FIG. 3 depicts an embodiment with an electromagnetic radiation emitter driving circuit 318 and certain types of identification devices 309, which do not require electrical connections between the base 305 and the control unit 325 to function. By way of example, and not as a limitation, in embodiments in which the identification device 309 is a device having an inductive load or a magnet the electrical contacts may not be necessary to verify the identification device 309. By bringing the base 305 into proximity to the control unit 325, the query module 308 may detect the presence or a characteristic of the identification device 309. More specifically, by way of example and not as a limitation, the query module 308 may measure the value of the inductive load or the magnetic field created by the identification device 309 contained within a base 305. The presence or an attribute of an identification device 309 in such a configuration may be the status of the identification device 309.

FIG. 5 depicts an embodiment with a ballast 510 and certain types of identification devices 509, which do not require electrical connections between the base 505 and the control unit 525 to function. By way of example, and not as a limitation, in embodiments in which the identification device 509 is a device having an inductive load or a magnet the electrical contacts may not be necessary to verify the identification device 509. By bringing the base 505 into proximity to the control unit 525, the query module 508 may detect the presence or a characteristic of the identification device 509. More specifically, by way of example and not as a limitation, the query module 508 may measure the value of the inductive load or the magnetic field created by the identification device 509 contained within a base 505. The presence or an attribute of an identification device 509 in such a configuration may be the status of the identification device 509.

Additional contacts may be present as required to activate the electromagnetic radiation emitter. In embodiments in which the electromagnetic radiation emitter emits x-rays, three electrical contacts and three electrical contact receptors may be required to drive the emitter. An additional two contacts and receptors may be required to communicate with the identification device. In embodiments in which the electromagnetic radiation emitter is to be driven utilizing other than a cold start method, it may be necessary to include four electrical contacts and four electrical contact receptors to drive the emitter. An additional two contacts and receptors may be required to communicate with the identification device.

FIG. 4 depicts a block diagram of the apparatus 400, in which a controller unit 425 is present. The control unit 425 may have a controller 407, which may comprise a query module 408 in electrical communication with the identification device 409 through third and fourth electrical contacts 403, 404 and third and fourth electrical contact receptors 428, 429. The control unit may comprise an electromagnetic radiation emitter driving circuit 418. The electromagnetic radiation emitter driving circuit 418 may output an electrical signal to the electromagnetic radiation emitter 417, which may energize the electromagnetic radiation emitter 417. The output of the electromagnetic radiation emitter driving circuit 418 may be provided to the first and second electrical contacts 401, 402 by the first and second electrical contact receptors 426, 427.

The query module 408 may control an electromagnetic radiation emitter driving circuit control signal sent to the electromagnetic radiation emitter driving circuit 418. The electromagnetic radiation emitter driving circuit 418 may output a voltage signal in response to a positive electromagnetic radiation emitter driving circuit control signal provided by the query module 408. The query module 408 may provide a negative electromagnetic radiation emitter driving circuit control signal to the electromagnetic radiation emitter driving circuit 418, preventing the electromagnetic radiation emitter driving circuit from outputting an energizing signal, and therefore preventing the electromagnetic radiation emitter 417 from emitting electromagnetic radiation, when the response received from the identification device 409 is not as anticipated. The query module 408 may provide a positive control signal to the electromagnetic radiation emitter driving circuit 418, causing the electromagnetic radiation emitter driving circuit 418 to output a voltage signal, or allowing the output of a voltage signal provided some other condition is met, when the response received from the identification device 409 indicates that the identification device 409 associated with the electromagnetic radiation emitter 417 is authorized.

Figure 6:
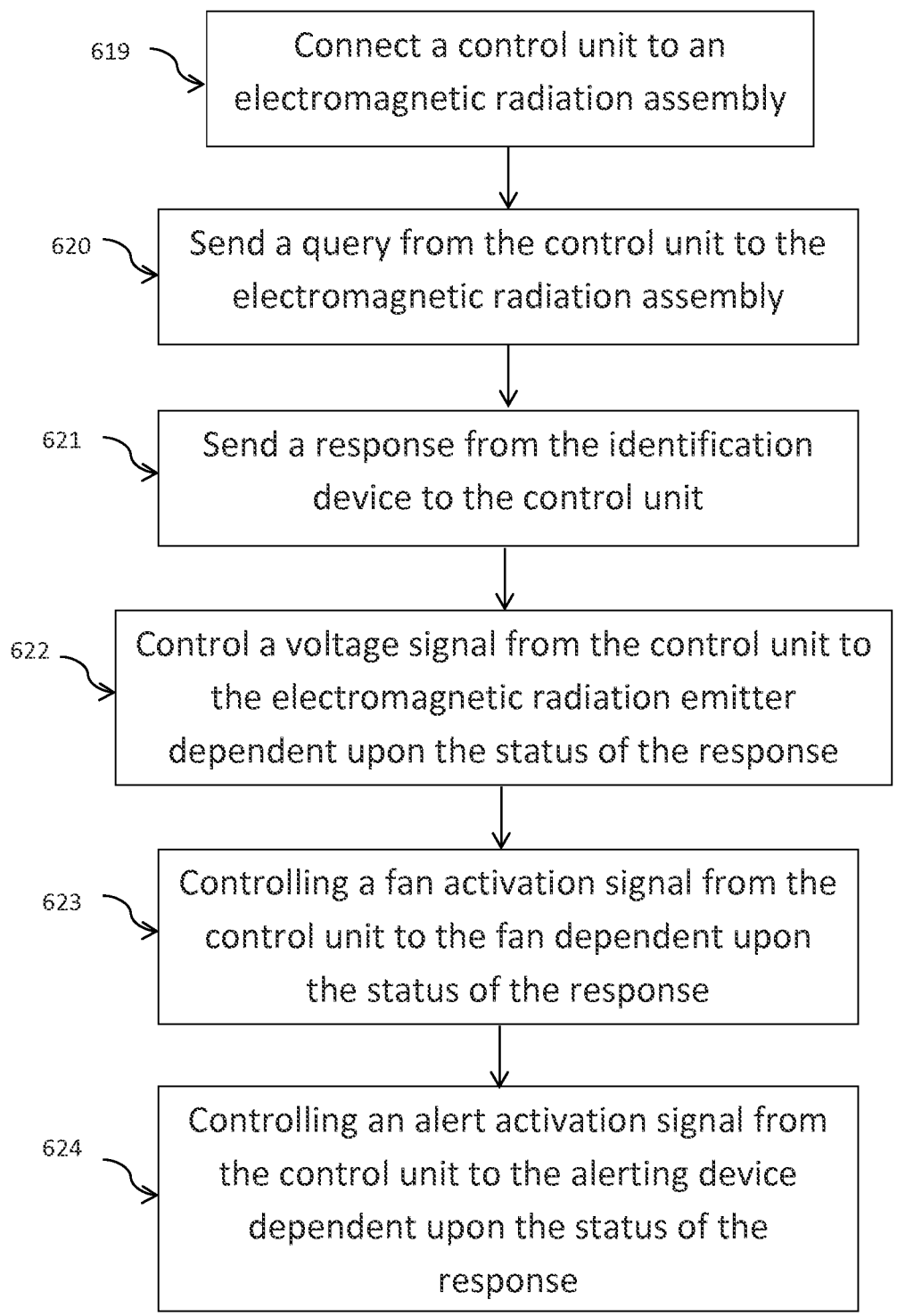
FIG. 6 is a flowchart of an inventive method.

Turning to FIG. 6, a method for activating and verifying an electromagnetic radiation assembly is described. A control unit is connected to the electromagnetic radiation assembly 619. The control unit sends a query to the electromagnetic radiation assembly 620. The query may be passive or active. In response to the query, the identification device, which is located on the electromagnetic radiation assembly, provides a response to the control unit 621. In embodiments in which the query is passive, the response may be the status of the identification device and may indicate the presence or absence of an identification device. The control unit may control the status of a voltage signal provided to an electromagnetic radiation emitter, which is part of the electromagnetic radiation assembly, dependent upon the status of the response that was received 622. By way of example, and not as a limitation, the control unit may activate a high voltage signal to a gas filled envelope, or other electromagnetic radiation emitter, when the response indicates that the electromagnetic radiation assembly is authorized. By way of another example, and not as a limitation, the control unit may prohibit a high voltage signal from activating the envelope in the event that the status of the response indicates that the electromagnetic radiation assembly is not authorized. By way of example, and not as a limitation, the control unit may activate a light emitting diode when the response indicates that the electromagnetic radiation assembly is authorized. By way of another example, and not as a limitation, the control unit may prohibit a voltage signal from activating a light emitting diode in the event that the status of the response indicates that the electromagnetic radiation assembly is not authorized.

The control unit may control a fan activation signal dependent upon the status of the response 623. By way of example, and not as a limitation, the fan activation signal may allow a fan to be activated and circulate the fluid about the electromagnetic radiation emitter, if the response indicates an authorized electromagnetic radiation device and prevent such activation otherwise.

The control unit may control an alert activation signal dependent upon the status of the response 624. By way of example, and not as a limitation, the alert activation signal may activate an alerting device if the response indicates an unauthorized electromagnetic radiation device.

The foregoing examples have been provided in the interest of clarity to illustrate an embodiment of the present invention in substantial detail. A person of skill in the art will appreciate that various electromagnetic emitting devices may be used with the present invention.

A person of skill in the art will appreciate that one or more of the above provided embodiments may be included in the operation of the electromagnetic radiation emitter of the present invention. Additionally, a person of skill in the art will appreciate additional embodiments that would be included within the scope and spirit of the present invention, after having the benefit of this disclosure. Furthermore, a skilled artisan will appreciate that the operations described above, along with additional operations that would be apparent to those in the art, may be performed exclusively, incrementally, sequentially, simultaneously, or any other operative configuration.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

What is claimed is:

1. An apparatus for emitting electromagnetic radiation comprising:
    at least one electromagnetic radiation emitter; and
    a base, further comprising:
        a first electrical contact in electrical communication with the at least one electromagnetic radiation emitter,
        a second electrical contact in electrical communication with the at least one electromagnetic radiation emitter,
        a third electrical contact,
        a fourth electrical contact, and
        an identification device in electrical communication with the third and fourth electrical contacts.

2. The apparatus according to claim 1 wherein the electromagnetic radiation emitter further comprises an envelope.

3. The apparatus according to claim 2 wherein the envelope contains low pressure mercury vapor.

4. The apparatus according to claim 1 wherein the at least one electromagnetic radiation emitter comprises at least one light emitting diode.

5. The apparatus according to claim 1 further comprising:
    a control unit further comprising:
        a first electrical contact receptor demountably engaging the first electrical contact,
        a second electrical contact receptor demountably engaging the second electrical contact,
        a third electrical contact receptor demountably engaging the third electrical contact,
        a fourth electrical contact receptor demountably engaging the fourth electrical contact, and
        a controller further comprising:
            a query module in electrical communication with the third and fourth electrical contact receptors;
            wherein the query module sends a query to the identification device and the identification device sends a response to the query module.

6. The apparatus according to claim 2 further comprising:
    a ballast, having an output, in electrical communication with the first and second electrical contact receptors and capable of applying a voltage across the first and second electrical contact receptors.

7. The apparatus according to claim 6 wherein the query module is in electrical communication with the ballast and wherein the query module controls the ballast output in accordance with the response.

8. The apparatus according to claim 5 further comprising:
    at least one alerting device, having an alert status, in electrical communication with the query module wherein the query module determines the alert status of the at least one alerting device in accordance with the response to the query.

9. The apparatus according to claim 5 further comprising:
    a fan in electrical communication with the query module wherein the query module provides a fan activation signal to the fan in accordance with the response to the query.

10. The apparatus according to claim 1 wherein the identification device comprises at least one electrical component having an electronic signature; and wherein the electronic signature is the response.

11. The apparatus according to claim 10 wherein the at least one electrical component comprises a silicon serial number chip; and
    wherein the electronic signature comprises a serial number.

12. The apparatus according to claim 10 wherein the at least one electrical component comprises an RC circuit; and wherein the electronic signature comprises a charge time.

13. The apparatus according to claim 10 wherein the at least one electrical component comprises an RC circuit; and
    wherein the electronic signature comprises a discharge time.

14. The apparatus according to claim 10 wherein the at least one electrical component comprises a circuit having a resistance value; and
    wherein the electronic signature comprises the resistance value.

15. The apparatus according to claim 10 wherein the at least one electrical component comprises a PROM; and
    wherein the electronic signature comprises a pre-programmed identifier.

16. The apparatus according to claim 6 wherein the ballast further comprises an arc controller configured to apply a voltage across the first and second electrical contact receptors thereby causing an electric arc in the envelope.

17. The apparatus according to claim 4 further comprising:
    an electromagnetic radiation emitter driving circuit, having an output, in electrical communication with the query module and capable of applying a voltage level to the first and second electrical contact receptors.

18. The apparatus according to claim 5 wherein the query module is in electrical communication with the electromagnetic radiation emitter driving circuit and wherein the query module controls the electromagnetic radiation emitter driving circuit output in accordance with the response.

19. An apparatus for emitting electromagnetic radiation comprising:

at least one electromagnetic radiation emitter;
a base, further comprising:
  a first electrical contact in electrical communication with the at least one electromagnetic radiation emitter,
  a second electrical contact in electrical communication with the at least one electromagnetic radiation emitter, and
  an identification device having a status; and
a control unit further comprising:
  a first electrical contact receptor,
  a second electrical contact receptor, and
  a controller further comprising:
    a query module capable of determining the status of the identification device;
  wherein the first electrical contact receptor demountably engages the first electrical contact, and
  the second electrical contact receptor demountably engages the second electrical contact.

20. The apparatus according to claim 19 wherein the electromagnetic radiation emitter further comprises an envelope.

21. The apparatus according to claim 20 wherein the envelope contains low pressure mercury vapor.

22. The apparatus according to claim 19 wherein the at least one electromagnetic radiation emitter comprises at least one light emitting diode.

23. The apparatus according to claim 20 further comprising:
  a ballast, having an output, in electrical communication with the first and second electrical contact receptors and capable of applying a voltage across the first and second electrical contact receptors.

24. The apparatus according to claim 23 wherein the query module is in electrical communication with the ballast and wherein the query module controls the ballast output in accordance with the status.

25. The apparatus according to claim 19 further comprising:
  at least one alerting device, having an alert status, in electrical communication with the query module wherein the query module determines the alert status of the at least one alerting device in accordance with the status.

26. The apparatus according to claim 19 further comprising:
  a fan in electrical communication with the query module wherein the query module provides a fan activation signal to the fan in accordance with the status.

27. The apparatus according to claim 19 wherein the identification device comprises at least one electrical component having an electronic signature; and wherein the electronic signature is the status.

28. The apparatus according to claim 27 wherein the at least one electrical component comprises an inductive load; and
  wherein the status comprises the presence of the inductive load.

29. The apparatus according to claim 27 wherein the at least one electrical component comprises a magnet having a magnetic field; and
  wherein the electronic signature comprises the presence of the magnetic field.

30. The apparatus according to claim 20 wherein the ballast further comprises an arc controller configured to apply a voltage across the first and second electrical contact receptors thereby causing an electric arc in the envelope.

31. The apparatus according to claim 22 further comprising:
  an electromagnetic radiation emitter driving circuit, having an output, in electrical communication with the query module and capable of applying a voltage level to the first and second electrical contact receptors.

32. The apparatus according to claim 22 wherein the query module is in electrical communication with the electromagnetic radiation emitter driving circuit and wherein the query module controls the electromagnetic radiation emitter driving circuit output in accordance with the status.

33. A method for activating and verifying an electromagnetic radiation assembly, the method comprising:
  electrically connecting a control unit to an electromagnetic radiation assembly further comprising an electromagnetic radiation device and a base, wherein the base further comprises an identification device;
  sending a query from the control unit to the identification device;
  sending a response having a status from the identification device to the control unit; and
  controlling an electromagnetic radiation device control signal from the control unit to the electromagnetic radiation device dependent upon the status of the response.

34. The method according to claim 33 further comprising:
  controlling a fan activation signal from the control unit to a fan dependent upon the status of the response.

35. The method according to claim 33 further comprising:
  controlling an alert activation signal from the control unit to an alerting device dependent upon the status of the response.

* * * * *